(12) United States Patent
Morikawa et al.

(10) Patent No.: US 6,727,094 B2
(45) Date of Patent: Apr. 27, 2004

(54) **CULTURED CELLS OF *RHAPHIOLEPIS UMBELLATA* THUNB. AND A METHOD FOR CULTURING TISSUES OF THE *RHAPHIOLEPIS UMBELLATA* THUNB. BY USING SAID CULTURED CELLS**

(75) Inventors: Hiromichi Morikawa, Higashihiroshima (JP); Misa Takahashi, Higashihiroshima (JP)

(73) Assignee: Hiroshima University, Higashihiroshima (JP)

( * ) Notice: Subject to any disclaimer, the term of this patent is extended or adjusted under 35 U.S.C. 154(b) by 4 days.

(21) Appl. No.: 10/058,067

(22) Filed: Jan. 29, 2002

(65) Prior Publication Data

US 2002/0137207 A1 Sep. 26, 2002

(30) Foreign Application Priority Data

Feb. 6, 2001 (JP) ........................ 2001-029613

(51) Int. Cl.$^7$ .................................. C12N 5/00
(52) U.S. Cl. ..................... 435/420; 435/410; 435/430.1
(58) Field of Search ................. 435/420, 410

Primary Examiner—Bruce R. Campell
Assistant Examiner—Susan B. McCormick
(74) Attorney, Agent, or Firm—Oliff & Berridge, PLC

(57) ABSTRACT

A cultured cell of *Rhaphiolepis umbellata* Thunb. having high differentiating power, said cultured cell being obtained by culturing a part of a tissue of the *Rhaphiolepis umbellata* Thunb. in a culture medium containing benzyladenine and naphthaleneacetic acid (NAA) in an amount effective to induce callus formation of the *Rhaphiolepis umbellata* Thunb.

8 Claims, No Drawings

CULTURED CELLS OF *RHAPHIOLEPIS UMBELLATA* THUNB. AND A METHOD FOR CULTURING TISSUES OF THE *RHAPHIOLEPIS UMBELLATA* THUNB. BY USING SAID CULTURED CELLS

BACKGROUND OF THE INVENTION (1) Field of the Invention

The present invention relates to cultured cells and a tissue-culturing method, and particularly the invention relates to cultured cells of *Rhaphiolepis umbellata* Thunb. and a method for culturing tissues of the *Rhaphiolepis umbellata* Thunb. by using said cultured cells.

(2) Related Art Statement

Recently, investigations have been vigorously carried out on the tissue culturing of the higher plants, and techniques for mass culturing plant tissues removed from leaves, stems, roots, etc. have public attracted attentions. When a plant piece cut off is place on agar or in a liquid containing a nutriment, a mass of cells swell up from a cut edge of the plant piece. This is called callus.

In general, cells of different tissues, for example, tissues of a root and a leaf, have different shapes and functions, respectively. This results from gradual differentiation during a time period in which the cells grow. However, the callus continue to grow without differentiation.

Generally, seeding or cutting-planting must be done so as to propagate plants. Further, the soil and the environment largely influence the growth of the plants. However, the culturing of the callus is not influenced by changes in these matters. In addition, the callus grows faster than ordinary plant bodies. When a hormone or a chemical substance that promotes germination or rooting is added to the callus, a complete plant body is obtained.

As such a callus tissue-culturing method, methods for culturing tissues of trees such as poplar and eucalyptus are known.

However, what has been established as the tissue-culturing methods are limited to the kinds of trees such as poplar and eucalyptus only. One of reasons for this is that it is difficult to grow or root other breeds unless appropriate hormones or the like are used.

The *Rhaphiolepis umbellata* Thunb., which is a plant belonging to the Rosaceae, is a roadside tree planted in a median strip of a road, etc. The *Rhaphiolepis umbellata* Thunb. is strong against the public pollution, and has saline resistance. In order to assuredly and swiftly provide such plants having strong public pollution resistance, the tissue-culturing method is effective. However, a method for stably mass propagating the *Rhaphiolepis umbellata* Thunb. has not been established.

SUMMARY OF THE INVENTION

It is an object of the present invention to provide cultured cells and a tissue-culturing method, which enable the establishment of stable mass propagation and transformation system of the *Rhaphiolepis umbellata* Thunb.

In order to accomplish the above object, the present inventors had repeatedly made strenuous investigations on conditions suitable for inducing the formation of callus and the redifferentiation of the *Rhaphiolepis umbellata* Thunb., and consequently have come to discover the cultured cells and the tissue-culturing method according to the present invention.

The cultured cell according to the present invention has high differentiating power, and is obtained by culturing a part of a tissue of the *Rhaphiolepis umbellata* Thunb. in a culture medium containing benzyladenine and naphthaleneacetic acid (NAA) in an amount effective to induce callus formation of the *Rhaphiolepis umbellata* Thunb.

In a preferred embodiment of the cultured cell of the *Rhaphiolepis umbellata* Thunb. according to the present invention, the tissue of the *Rhaphiolepis umbellata* Thunb. is a tissue selected from the group consisting of a shoot apex, a stem, a leaf, an embryonic cell and a root.

In another preferred embodiment of the cultured cell of the *Rhaphiolepis umbellata* Thunb. according to the present invention, the tissue of the *Rhaphiolepis umbellata* Thunb. is a tissue originated from a plant body raised from a seedling obtained by germinating a sterilized seed of the *Rhaphiolepis umbellata* Thunb.

In a further preferred embodiment of the cultured cell of the *Rhaphiolepis umbellata* Thunb. according to the present invention, the tissue of the *Rhaphiolepis umbellata* Thunb. is a tissue less than 2 weeks after seeding the *Rhaphiolepis umbellata* Thunb.

In a still further preferred embodiment of the cultured cell of the *Rhaphiolepis umbellata* Thunb. according to the present invention, the tissue of the *Rhaphiolepis umbellata* Thunb. is a tissue obtained by aseptically growing a seed of the *Rhaphiolepis umbellata* Thunb.

In a still further preferred embodiment of the cultured cell of the *Rhaphiolepis umbellata* Thunb. according to the present invention, the culture medium is a WP culture medium or an MS culture medium.

The method for culturing a tissue of a *Rhaphiolepis umbellata* Thunb. according to the present invention comprises the steps of subculturing any of the above cultured cells in a culture medium containing benzyladenine and naphthaleneacetic acid (NAA) in an amount effective to induce callus formation of the *Rhaphiolepis umbellata* Thunb., and thereby obtaining plantlet of the *Rhaphiolepis umbellata* Thunb.

In a preferred embodiment of the *Rhaphiolepis umbellata* Thunb. tissue-culturing method according to the present invention, the culture medium is a WP culture medium or an MS culture medium.

The cultured cell according to the present invention is a cultured cell of the *Rhaphiolepis umbellata* Thunb. having high differentiating power, said cultured cell being obtained by culturing a part of a tissue of the *Rhaphiolepis umbellata* Thunb. in a culture medium containing benzyladenine and naphthaleneacetic acid (NAA) in an amount effective to induce callus formation of the *Rhaphiolepis umbellata* Thunb. In general, the plantlet is formed according to the tissue-culturing method in the course of (1) formation of the callus, (2) formation of a polyblast, (3) redifferentiation of the polyblast and (4) formation of the plantlet. The tissue culturing of the *Rhaphiolepis umbellata* Thunb. takes this formation course. Here, the term "polyblast" means a mass of numerous shoots in which cells are differentiated.

In the following, the cultured cells of *Rhaphiolepis umbellata* Thunb. and the tissue-culturing method therefor according to the present invention will be explained.

Although the tissues of the *Rhaphiolepis umbellata* Thunb. are not particularly limited, tissues from stems, leaves, roots, stem apexes, root apexes, embryonic cells, etc. may be recited. Stems, leaves, roots, stem apexes, embryonic cells and roots are preferred.

The tissues of the *Rhaphiolepis umbellata* Thunb. may be ones taken from a matured tree of the *Rhaphiolepis umbellata* Thunb. Preferably, the tissue is a tissue originated from a relatively young cell tissue obtained after seeding the *Rhaphiolepis umbellata* Thunb. For example, the tissue obtained 2 weeks, more preferably less than 9 to 10 days, after seeding the *Rhaphiolepis umbellata* Thunb.

Seeds of the *Rhaphiolepis umbellata* Thunb. can be aseptically germinated and grown on the culture medium. The aseptic treatment for the cutting is not particularly limited, for example, such a treatment can be effected by treating the tissue with ethanol or the like for a few or several hours and with sodium hypochlorite for a few or several hours and is washed with sterilized water. It is preferable to use a seed fed with water at 4 to 10° C. in dark for not less than 1 to 3 nights.

The cultured cells of the present invention can be obtained by culturing a part of the tissue as mentioned above, in a culture medium containing benzyladenine and naphthaleneacetic acid (NAA) in an amount effective to induce callus formation of the *Rhaphiolepis umbellata* Thunb. The amount of benzyladenine depends upon the culture medium used and the culturing condition, and is preferably 0.5 to 10.0 μM, more preferably 0.5 to 5.0 μM. The reason for this range is to enhance the redifferentiation percentage. The amount of naphthaleneacetic acid (NAA) is not particularly limited, but is preferably 0.1 to 1 μM. The reason for this range is also to enhance the redifferentiation percentage.

As the culture medium, culture media such as a WP culture medium, an MS culture medium, a white culture medium and a modified culture medium may be recited. The WP culture medium is a cultured medium obtained by improving the MS culture medium for the purpose of the stem-tip culturing and mass culturing of ericaceous Kalmia latiflora. The MS culture medium is a culture medium developed aiming at the propagation of the marrow tissues and the callus of tobacco. In culturing the *Rhaphiolepis umbellata* Thunb., the WP culture medium is preferred from the standpoint of enhancing the callus formation rate and the redifferentiation percentage.

In addition, the culture medium may contain trace amounts of organic substances, carbonaceous sources, etc. usually used in culturing. As the organic substances used in a trace amount, vitamins B1, B6, other vitamins such as nicotine acid, thiamine hydrochloride, and pyridoxine hydrochloride, etc.; amino acids such as glycin, asparagine, etc.; hexavalent alcohols such as inosital, sorbit, etc. may be used.

As the carbonaceuous source, saccharides such as sucrose, glycose, etc.; may be recited.

The tissue piece planted in the culture medium can be cultured in a bright condition or a dark condition in a temperature range of 22 to 28° C. The temperature condition is preferably 24 to 26° C. Callus begins to be formed about one week after the culturing, and the callus is completely formed about 3 to 4 weeks after the culturing. The stable callus is obtained by subculturing at a subculturing interval of about 10 to 20 days.

According to the tissue-culturing method of the present invention, a plantlet of the *Rhaphiolepis umbellata* Thunb. can be obtained by subculturing the cultured cell having high differentiating power in a culture medium containing benzyladenine and naphthaleneacetic acid (NAA) in an amount effective to induce callus formation of the *Rhaphiolepis umbellata* Thunb. As to the amounts of benzyladenine (TDZ) and naphthaleneacetic acid (NAA), the above-mentioned condition employed in culturing the cultured cells can be used.

As the cultured cells of the *Rhaphiolepis umbellata* Thunb. having high differentiating power, the above-mentioned cultured cells according to the present invention can be used.

The growth of the plantlet can be promoted by cutting out a polyblast and coating its cut edge with indoleacetic acid, for example.

As a support for the culture medium, pearlite, vermiculite, Gellan Gum, agar, agarose, etc. may be recited.

EXPERIMENTS

The present invention will be explained below in more detail based on experiments, but the invention is not to be interpreted as being limited to the following examples.

Experiment 1

A culture medium in which the MS culture medium or the WP culture medium was used as a fundamental culture medium and 1% sucrose and 0.3% Gellan Gum were added as the carbonaceuous source and a gelling agent, respectively, was used.

Cut pieces, 0.5~1 mm long, were prepared from leaf, shoot and root tissues of the *Rhaphiolepis umbellata* Thunb. asepatically germinated, implanted and cultured on a culture medium to which were added benzyladenine and/or naphthaleneacetic acid (NAA) as plant hormones. One month after the implanting, it was observed that polyblasts were formed from the cut pieces. The polyblasts were cut out, their cut edge were coated with iondoleacetic acid, and the polyblasts were implanted into the above culture medium or a culture containing pearlite and vermiculite, and allowed to take roots.

The small plant bodies in which growth of the roots were observed were used as a sapling.

Cut pieces of stems of the *Rhaphiolepis umbellata* Thunb. were ultured on the culture medium to which benzyladenine and/or aphthaleneacetic acid (NAA) were adde. Table 1 shows numbers of the cut pieces for which the formation of polyblast was observed and the umber of shoots observed.

TABLE 1

| NAA (μM) | benzyladenine (μM) | Number of cut piece* | Number of shoots/ cut piece |
|---|---|---|---|
| 0.1 | 0.5 | 19 | 4 |
| 0.2 | 0.5 | 19 | 3 |
| 0.5 | 0.5 | 24 | 2.9 |
| 1.0 | 0.5 | 20 | 0 |
| 0.1 | 1.0 | 15 | 2.3 |
| 0.2 | 1.0 | 22 | 2.8 |
| 0.5 | 1.0 | 14 | 2 |
| 1.0 | 1.0 | 23 | 0 |
| 0.1 | 2.0 | 14 | 2.5 |
| 0.2 | 2.0 | 26 | 2.9 |
| 0.5 | 2.0 | 12 | 2 |
| 1.0 | 2.0 | 24 | 0 |
| 0.1 | 5.0 | 22 | 2.2 |
| 0.2 | 5.0 | 24 | 2.4 |
| 0.5 | 5.0 | 26 | 0 |
| 1.0 | 5.0 | 18 | 0 |

*(Number of cut pieces for which the formation of polyflasts was observed) × 30/cut piece The cultured cells according to the present invention exhibit the advantageous effects that the tissue culturing of the *Rhaphiolepis umbellata* Thunb. can be effectively performed and that the plant bodies having high differentiating power can be reproduced.

Further, the tissue-culturing method according to the present invention exhibits the advantageous effects that the *Rhaphiolepis umbellata* Thunb. can be stably mass propagated and that the method can be used for the growth of the transformed plant bodies.

What is claimed is:

1. A cultured cell of *Rhaphiolepis umbellata* Thunb., said cultured cell being obtained by culturing a part of a tissue of the *Rhaphiolepis umbellata* Thunb. in a culture medium containing at least one of benzyladenine and naphthaleneacetic acid (NAA) in an amount effective to induce callus formation of the *Rhaphiolepis umbellata* Thunb.

2. The cultured cell set forth in claim 1, wherein the tissue of the *Rhaphiolepis umbellata* Thunb. is a tissue selected from the group consisting of a shoot apex, a stem, a leaf, an embryonic cell and a root.

3. The cultured cell set forth in claim 1, wherein the tissue of the *Rhaphiolepis umbellata* Thunb. is a tissue originated from a plant body raised from a seedling obtained by germinating a sterilized seed of the *Rhaphiolepis umbellata* Thunb.

4. The cultured cell set forth in claim 1, wherein the tissue of the *Rhaphiolepis umbellata* Thunb. is a tissue obtained by aseptically growing a seed of the *Rhaphiolepis umbellata* Thunb.

5. The cultured cell set forth in claim 1, wherein the tissue of the *Rhaphiolepis umbellata* Thunb. is a tissue that is less than 2 weeks old after seeding the *Rhaphiolepis umbellata* Thunb.

6. The cultured cell set forth in claim 1, wherein the culture medium is a WP culture medium or an MS culture medium.

7. A method for culturing a tissue of a *Rhaphiolepis umbellata* Thunb., comprising the steps of subculturing the cultured cell set forth in claim 1 in a culture medium containing benzyladenine and naphthaleneacetic acid (NAA) in an amount effective to induce callus formation of the *Rhaphiolepis umbellata* Thunb., and thereby obtaining a plantlet of the *Rhaphiolepis umbellata* Thunb.

8. The method set forth in claim 7, wherein the culture medium is a WP culture medium or an MS culture medium.

* * * * *